United States Patent [19]

Fukuyo

[11] Patent Number: 4,468,201
[45] Date of Patent: Aug. 28, 1984

[54] DENTAL ENDOSSEOUS IMPLANTS

[76] Inventor: Sekio Fukuyo, 41-6, 1-chome, Shinsakae, Naka-ku, Nagoya-shi, Aichi-ken, Japan

[21] Appl. No.: 503,901

[22] Filed: Jun. 13, 1983

[30] Foreign Application Priority Data

Jul. 7, 1982 [JP] Japan ................................ 57-118181

[51] Int. Cl.³ ............................................... A61C 8/00
[52] U.S. Cl. ...................................................... 433/176
[58] Field of Search ................................ 433/173, 176

[56] References Cited

U.S. PATENT DOCUMENTS 3,729,825  5/1973  Linkow ................................ 433/176

Primary Examiner—Robert Peshock
Attorney, Agent, or Firm—Browdy & Neimark

[57] ABSTRACT

An endosseous implant structure for oral implantology, comprising a planar body portion embedded in an alveolar bone to form an artificial tooth root, at least one neck portion extending from one end of the planar body portion in a direction substantially parallel to the plane of the body portion, and at least on head portion extending from one end of the neck portion remote from the body portion and projecting into a oral cavity to form an abutment for an artificial tooth. The planar body portion includes a plurality of leg portions defined by cutouts formed in the body portion. At least the leg portions are made of a metal material exhibiting a thermal shape memory effect of deformation in response to variation in temperature thereof. The leg portions are deformed sidewise and away from the plane of the body portion upon temperature variation after insertion of the body portion into the alveolar bone.

16 Claims, 12 Drawing Figures

FIG. 1
FIG. 2
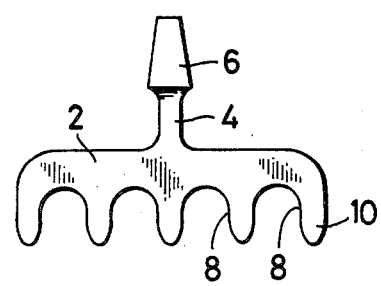
FIG. 3  FIG. 4  FIG. 5
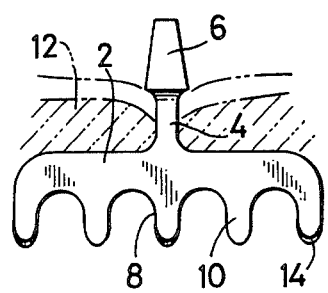
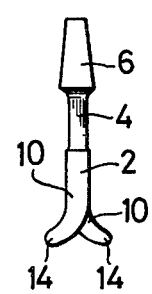
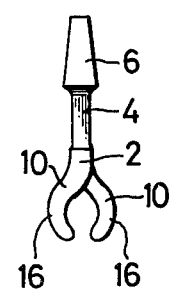
FIG. 6  FIG. 7
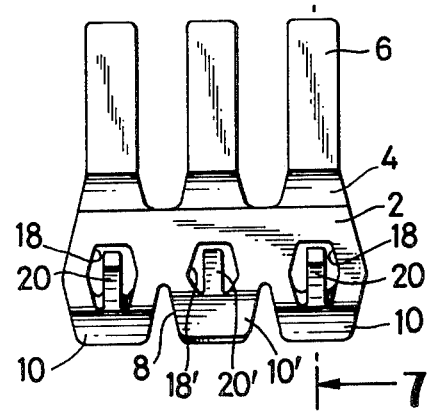
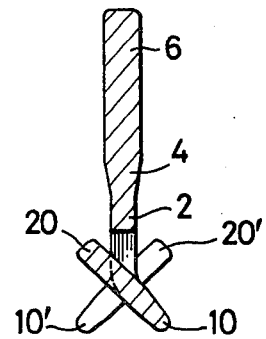

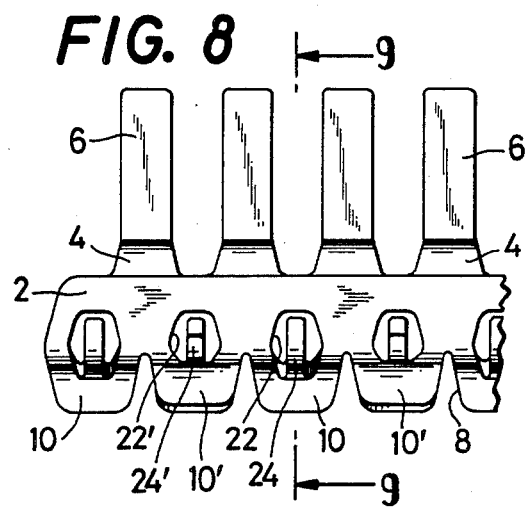
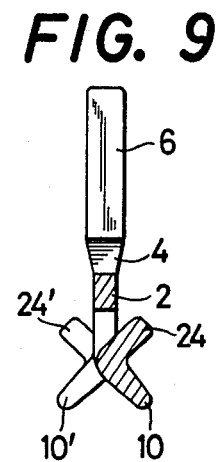
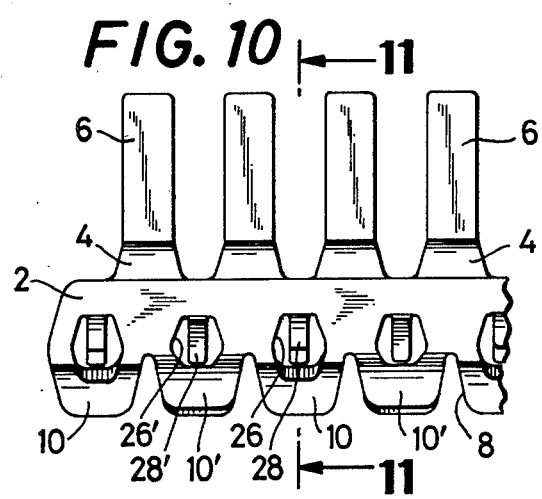
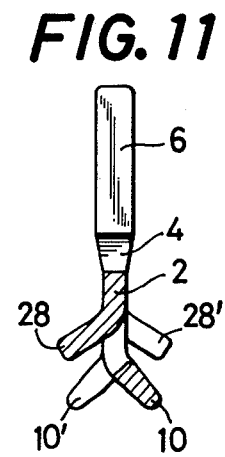
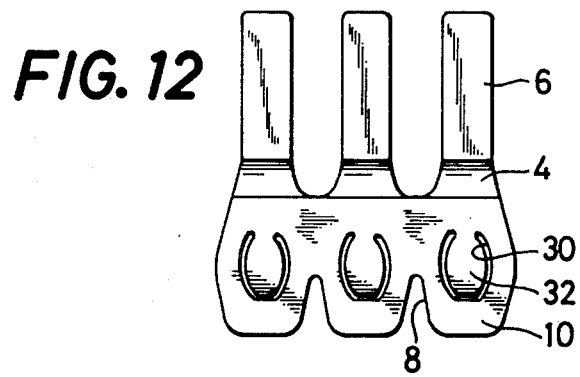

DENTAL ENDOSSEOUS IMPLANTS

BACKGROUND OF THE INVENTION

The present invention relates generally to oral implantology, and more particularly to improved dental endosseous implant structures which are easily inserted in and retained by an alveolar bone or dentale, having a high resistance to sinking, tipping and displacement.

In the art of the oral implantology, an endosseous implant is know according to U.S. Pat. No. 3,729,825, wherein an integral metal structure of the blade type implant comprises a wedge-shaped implant body portion inserted in the alveolar bone as artificial tooth roots or fangs, a head portion extending from the body portion and projecting in the oral cavity as a base for artificial teeth or dentes, and a neck portion connecting the implant body portion and the head portion.

Such endosseous implant is fabricated of a thin plate which generally has a thickness of as small as 1.1–1.3 mm so that the insertion of the implant in the alveolar bone structure is facilitated. On the other hand, however, such implant tends to sink or tip in the avleolar bone during service of an artificial tooth or denture due to its occlusal force, thus suffering some drawbacks in terms of retention and durability thereof. Another disadvantage of the prior implant of a thin planar material is its tendency of lateral inclination with respect to the aveolar bone structure because of its thickness, which can not exceed an ordinary thickness of 3–4 mm of the aveolar bone as measured at its end on the side of oral cavity, otherwise the insertion of the blade implant into the bone structure is difficult.

SUMMARY OF THE INVENTION

The present invention was developed in view of the above discussed situation in the art of endosseous implantology. It is accordingly an object of the present invention to provide a dental endosseous implant structure which is easily inserted or seated in the alveolar bone and capable of providing a high resistance to displacement thereof such as sinking or subsidence and tipping or inclination.

According to the present invention, there is provided an endosseous implant structure for oral implantology, which comprises a planar body portion embedded in an alveolar bone to form an artificial tooth root, at least one neck portion extending from one end of the planar body portion in a direction substantially parallel to the plane of the body portion, and at least one head portion extending in said direction from one end of the neck portion remote from the body portion and projecting into a oral cavity to form an abutment for an artificial tooth. The planar body portion includes a plurality of leg portions defined by cutouts formed in the body portion. At least the leg portions are made of a metal material exhibiting a thermal shape memory effect of deformation in response to variation in temperature thereof. The leg portions are deformed sidewise, and away from said plane, of the body portion upon the temperature variation after insertion of the body portion into the alveolar bone.

The endosseous implant structure provided according to the invention comprises a leg portion fabricated of a thermal shape memory material which is changed in configuration upon variation in temperature thereof. Thus, the implant structure is adapted to have a planar or blade-like configuration before insertion thereof in the alveolar bone so that its insertion is facilitated, but after the insertion thereof its shape memory effect will arise, i.e., its shape is varied so as to form a large-sized artificial tooth root or fang which is highly resistant to sinking and/or tipping in the aveolar bone structure. The endosseous implant structure of the invention is further advantageous in that its small thickness assures an extreme ease of dental surgery for inserting and retaining the implant in the avelolar bone structure.

BRIEF DESCRIPTION OF THE DRAWINGS

The above and other objects, features and advantages of the present invention will become more apparent from reading the following description of the preferred embodiments taken in connection with the accompanying drawings in which:

FIG. 1 is a front elevational view of one embodiment of a dental endosseous implant structure of the invention before it is inserted into the alveolar bone, i.e., when it is placed at a lower temperature;

FIG. 2 is a side elevational view of the implant structure of FIG. 1;

FIG. 3 is a front elevational view, partly in cross section, showing the implant structure inserted in the alveolar bone, which has reverted to its original shape at a higher temperature;

FIG. 4 is a side elevational view of the implant structure of FIG. 3;

FIG. 5 is a side elevational view, corresponding to FIG. 4, showning another embodiment of the invention wherein the shape recovered through shape memory effect is different from that of FIG. 4;

FIG. 6 is a front elevational view of a further embodiment of an implant structure of the invention which has reverted to its original shape upon heat application thereto;

FIG. 7 is a side elevational view in cross section of the implant structure taken along line 7—7 of FIG. 6;

FIG. 8 is a view of another embodiment of the invention corresponding to FIG. 6, and FIG. 9 is a cross sectional view taken along line 9—9 of FIG. 8;

FIG. 10 is a view of a still further embodiment of the invention corresponding to FIGS. 6 and 8, and FIG. 11 is a cross sectional view taken along line 11—11 of FIG. 10; and FIG. 12 is a front elevational view showing still another embodiment of the invention corresponding to FIG. 1.

DETAILED DESCRIPTION OF THE PREFERRED EMBODIMENTS

Referring to the accompanying drawings, preferred embodiments of the invention are described in detail.

There is shown in FIGS. 1 and 2 one form of an endosseous implant structure according to the invention. The implant structure comprises an implant body portion 2 of planar wedge-shaped configuration which serves as an artificial tooth root or fang, a neck portion 4 extending from one end of the body portion 2 in a direction substantially parallel to the plane of the body portion, and a head portion 6 extending further from one end of the neck portion 4 remote from the body portion 2. The head portion 6 will be exposed within a oral cavity (as shown in FIG. 3) to serve as a tooth abutment for an artificial tooth or denture. The implant body portion 2 comprises a plurality of leg portions 10 which are defined by vents or cutouts 8 provided on one side thereof remote from the neck portion 4. As shown in FIG. 3, these leg portions 10 are embedded, together with the body and neck portions 2 and 4, in the alveolar bone structure 12 so as to act as artificial fangs to bear an occlusal force exerted to the head portion 6.

The implant structure embodying the present invention is at least partially made of alloys such as Ti—Ni, Ni—Al, Cu—Zn, In—Tl, Fe—Pd, Cu—Al—Ni, and Cu—Zn—Al which have a thermal shape memory effect. In general, the phenomenon of "one-way" shape memory effect arises because a specimen alloy which has been deformed from its determinate shape at a lower temperature will revert to the original determinate shape on heating to a higher temperature, but the shape to which the alloly has been deformed at the lower temperature will not be recovered by re-cooling the alloy back to that lower temperature.

Of all the portions of the implant structure shown in FIGS. 1 and 2, viz., body portion 2, neck portion 4 and head portion 6, at least the leg portions 10 of the body portion 2 are made of the above indicated shape memory alloys. These leg portions 10 which assume a shape as illustrated in FIGS. 1 and 2 at a lower temperature, have memory shapes shown in FIGS. 3 and 4 or 5, which memory shapes are presented when they are placed at a temperature of a living body or a temperature slightly higher than the body temperature. More specifically stated, the leg portions 10 having the memory shapes will be deformed normal to the plane of the body portion 2 or across the thickness thereof such that the individual portions 10 are displaced away from each other in alternately opposite directions in the form of saw teeth. The thermal deformation of the leg portions 10 may cause the free ends 14 thereof to be displaced away from the body portion 2 so as to protrude sidewise of the body portion in opposite directions as illustrated in FIG. 4, or cause the central part 16 of the leg portions to be displaced away from the body portion 2 in opposite directions so as to present an arcuate outwardly curved shape as shown in FIG. 5.

The implant structure constructed as described above is inserted in the alveolar bone 12 while it is kept in its planar shape at a predetermined low temperature. After the leg portions 10 have been embedded in the alveolar bone 12 as shown in FIG. 3, their temperature is elevated by a body heat to the body temperature, or to a temperature slightly higher than the body temperature by external heat conduction or by electrical heating or other means. As a result, the leg portions 10 will be deformed sidewise alternately in opposite directions as illustrated in FIGS. 4 and 5 due to the thermal shape memory characteristics of a shape memory alloy, that is, the shape memory effect which permits the leg portions 10 to revert to its original shape upon heating to a higher temperature. It is preferable that such thermal deformation of the leg portions 10 do not proceed abruptly in an initial period of the thermal recovery of the original shape, but take place gradually or slowly for a longer period of time. It is also noted that the alveolar bone or dentale 12 is biologically re-composed in response to change in configuration of the leg portions 10 so as to provide a support structure suitable for the deformed leg portions 10, this type of endosseous implants being therefore referred to as "bone-adaptive type" endosseous implants.

As discussed above, the endosseous implant structure of the invention is very easy to be inserted into a recess or groove formed in the alveolar bone because the body portion including the leg portions 10 assumes a planar shape before they are inserted, while at the same time the structure is sturdy after insertion or seating thereof thanks to the thermal shape memory deformation of the leg portions 10 which provides an effect similar to that obtained from an increase in thickness of the body portion 2 which is actually a thin planar body. In other words, the thermal deformation of the leg portions will increase a force receiving area of the leg portions in the aveolar bone, thereby providing a high resistance to the tendency of the implant to sink or subside in the bone structure due to occlusal forces exerted through an artificial tooth. Further, the implant structure of the invention is highly resistant to its tendency to tip or incline in the bone structure, thereby effectively improving the durability of artificial dens.

Thus, the present invention has made it possible to insert a large-sized implant which has been found absolutely impossible through a conventional method of forming a recess in the alveolar bone. The previously indicated thermal shape memory effect will eventually provide an increase in the size of the leg portions which is effective in preventing their sinking and tipping, thereby allowing the artificial tooth to serve for a prolonged perfiod and facilitating the surgical operation for installation of the endosseous implant.

While in the above disclosed embodiment the leg portions 10 are adapted to deflect, through variation in temperature, in alternately opposite directions away from the body portion 2 normal to the plane thereof, the deformation of the leg portions 10 through the shape memory effect is not limited thereto, but may be modified so that the leg portions deflect in other directions, for example, in obliquely diverging directions or they are twisted in suitable directions. Further, the leg portions 10 whose free ends 14 or central parts 16 are displaced sidewise of the body portion 2 in the preceding embodiments, may be adapted so that other parts of the portion 2 are displaced relative to the body portion 2 within the principle of the invention wherein the body portion 2 is given a memory shape which results in formation of a large-sized artificial tooth root and resultant increase in resistance thereof to the tendency of sinking and tipping of the root. It is further appreciated to adopt various other features of thermal deformation of the shape memory metal material than described above, which are known in the art.

It is also appreciated that the implant structure has more than two head portions each extending from a neck portion to provide plural tooth abutments, as illustrated in FIGS. 6, 8, 10 and 12 which show different embodiments of the present implant structures when they are subject to a shape memory effect at a higher temperature. In those figures and FIGS. 7, 9 and 11, the same reference numerals will be used to identify the parts which correspond to those of the implant structures shown in the preceding figures.

The implant structures of FIGS. 6 through 12 which have plural neck portions 4 and corresponding head portions 6, are different from the previously discussed structures also in the construction of the body portion 2, as described below in detail.

The body portion 2 of the implant structure of FIGS. 6 and 7 has three generally U-shaped (shape of inverted letter "U" in FIG. 6) cutouts or slots 18, 18', 18 corresponding to leg portions 10, 10', 10 which are provided in aligned with the corresponding neck and head portions 4, 6 in a direction across the width of the body portion 2. Each of the slots 18, 18' defines a tongue 20, 20' which has the free upper end and the fixed lower end terminating in the leg portion 10, 10'. While the prime numbers are used to indicate the centrally located leg portion 10', slot 18' and tongue 20', they are identical to the counterparts 10, 18 and 20 located on both sides thereof. The prime numbers are used for easy understanding of a shape memory effect of the structure.

The leg portions 10, 10' and the tongues 20, 20' are deformed upon heat application such that the leg portions 10, 10' are displaced sidewise in alternately opposite directions as previously discussed, and at the same time, the corresponding tongues 20, 20' integral with the leg portions 10, 10' are moved together with the same so that the integral member of the leg portion and the tongue is pivoted a predetermined angle substantially about the fixed end of the tongue with respect to the plane of the body portion 2, as clearly shown in FIG. 7. More particularly described, the tongue 20 on the right side of the structure as seen in FIG. 6, for example, is displaced such that its free end is moved away from the plane of the body portion 2 in the direction opposite to that in which the free end of the leg portion 10 is displaced in the plane normal to the body portion 2. In the meantime, the central leg portion 10' and tongue 20' are pivoted similarly, but in a direction opposite to that in which the right leg portion 10 and tongue 20 are pivoted, so that the integral member 10', 20' is disposed in crossed relation with the integral member 10, 20, and with the left leg portion 10 and tongue 20. Thus, the leg portions 10, 10' are deformed in opposite directions, and accordingly the corresponding tongues 20, 20' are displaced also in opposite directions.

Another form of implant structure shown in FIGS. 8 and 9 is different from that of FIGS. 6 and 7 in that the leg portions 10, 10' are arranged so that each of them is located between extension lines of the corresponding head portions 6. Therefore, tongues 24, 24' defined by generally U-shaped slots 22, 22' are also located between the said extension lines. Another difference of this form of implant structure lies in the memory shape which is recovered at a higher temperature. Namely, the tongue 24 is deformed on the same side of the body portion 2 such that it extends obliquely upward in "dog-leg" relation with the leg portion 10 which extends obliquely downward, or such that the leg portion 10 and the tongue 24 diverge at the fixed end of the tongue 24, as illustrated in FIG. 9. As in the above embodiment, the leg portion 10' and the corresponding tongue 24' adjacent to the counterparts 10 and 24 are deformed on the opposite side of the body portion 2 to provide a crossed configuration in the aveolar bone. In this embodiment, the thermal shape memory effect of the leg portion 10, 10' allows the above deformation of the tongue 24, 24' with respect to the leg portion.

FIGS. 10 and 11 show a further embodiment of the implant structure which is different from the preceding embodiment of FIGS. 8 and 9 in that U-shaped slots 26, 26' are formed so as to define tongues 28, 28' each of which has the fixed upper end and the lower end extending toward the free end of the leg portion 10, 10'. As shown in FIG. 11, upon heat application, the adjacent leg portions 10 and 10' are displaced on opposite sides of the body portion 2. Similarly, the adjacent tongues 28 and 28' are deformed on the opposite sides. It is noted, however, that the deformation of the tongue 28, for example, takes place on the side opposite to the side on which the corresponding leg portion 10 is deformed. This relation is also applicable to the combination of the leg portion 10' and the tongue 28'. Thus, this arrangement provides a "walking-man" configuration in the aveolar bone, as illustrated in FIG. 11. It is possible that the tongue 28, 28' is displaced on the same side of the body portion 2 as the leg portion 10, 10'. In this instance, too, the "walking man" configuration in cross section is established. As is apparent from the foregoing description of the operation, the instant embodiment requires that at least the portions of the body portion 2 adjacent to the fixed end of the tongues 28, 28', as well as the leg portions 10, 10' be made of a shape memory alloy.

While generally U-shaped cutouts or slots are formed in the body portion 2 to define substantially rectongueular tongues in the previous embodiments, such slots and tongues are not limited to those shown in FIGS. 6–11. For example, the tongues 20, 24, 28 may be replaced by an oval tongue 32 which is defined by a different form of U-shaped slot 30 having arcuate arms, as illustrated in FIG. 12.

It is to be understood that various other modifications and improvements of the invention may be made to those skilled in the art without departing from the scope of the invention which is defined by the appended claims.

What is claimed is:

1. An endosseous implant structure for oral implantology, comprising:
    a planar body portion embedded in an alveolar bone to form an artificial tooth root;
    a least one neck portion extending from one end of said planar body portion in a direction substantially parallel to the plane of the body portion; and
    at least one head portion extending in said direction from one end of said at least one neck portion remote from said body portion and projecting into a oral cavity to form an abutment for an artificial tooth;
    said planar body portion including a plurality of leg portions defined by cutouts formed in said body portion, at least said leg portions being made of a metal material exhibiting a thermal shape memory effect of deformation in response to variation in termperature thereof, said leg portions being deformed sidewise, and away from said plane, of said body portion upon the temperature variation after insertion of said body portion into the alveolar bone.

2. An endosseous implant structure as recited in claim 1, wherein said leg portions are thermally displaced normal to said plane of said body portion and in alternately opposite directions so as to move away from each other.

3. An endosseous implant structure as recited in claim 1, wherein said leg portions assume thermally recoverable memory shapes causing one of a free end and a central part thereof to be displaced sidewise of said body portion.

4. An endosseous inplant structure as recited in claim 1, wherein said thermal shape memory effect arises when the temperature of said body portion is elevated to a temperature higher than that before said body portion is inserted in the alveolar bone.

5. An endosseous implant structure as recited in claim 1, wherein said metal material is selected from a group consisting of Ti—Ni, Ni—Al, Cu—Zn, In—Tl, Fe—Pd, Cu—Al—Ni, and Cu—Zn—Al.

6. An endosseous implant structure as recited in claim 1, which is entirely made of said metal material exhibiting a thermal shape memory effect of deformation.

7. An endosseous implant structure as recited in claim 1, wherein said planar body portion has a plurality of slots which define a corresponding number of tongues corresponding to said plurality of leg portions, each of said tongues being disposed in parallel to said plane of said body portion prior to said temperature variation, said each tongue being deformed sidewise, and away from said plane, of said body portion upon said temperature variation.

8. An endosseous implant structure as recited in claim 7, wherein said slots and tongues are aligned with said leg portions in a direction across the width of said body portion.

9. An endosseous implant structure as recited in claim 8, wherein said at least one head portion is provided in plural number, said leg portions being aligned with the head portions in said direction.

10. An endosseous implant structure as recited in claim 8, wherein said at least one head portion is provided in plural number, said leg portions being disposed between extension lines of the head portions.

11. An endosseous implant structure as recited in claim 7, wherein said each tongue has a lower end terminating in respective one of said leg portions.

12. An endosseous implant structure as recited in claim 11, wherein said tongue is pivoted with said respective leg portion substantially about said lower end of the tongue upon said temperature variation such that said tongue is in line with said leg portion.

13. An endosseous implant structure as recited in claim 11, wherein said tongue and said respective leg portion diverge from said plane on the same side thereof upon said temperature variation.

14. An endosseous implant structure as recited in claim 7, wherein said each tongue has an upper fixed end and a lower end extending toward a free end of respective one of said leg portions, at least portions of said body portion adjacent to said upper fixed end of the tongue as well as said leg portions being made of said metal material exhibiting a thermal shape memory effect.

15. An endosseous implant structure as recited in claim 14, wherein said tongue is deformed, upon said temperature variation, on the side of said body portion opposite to that on which said respective leg portion is deformed.

16. An endosseous implant structure as recited in claim 7, said slots are generally U-shaped.

* * * * *